United States Patent
Kowalski et al.

(10) Patent No.: US 12,303,160 B2
(45) Date of Patent: May 20, 2025

(54) DEPLOYABLE DYNAMIC STENT AND ADJUSTABLE CUTTING JET DEVICE

(71) Applicant: Hydrocision, Inc., North Billerica, MA (US)

(72) Inventors: Paul Kowalski, North Billerica, MA (US); Alain Tranchemontagne, North Billerica, MA (US); Duane Couri, North Billerica, MA (US)

(73) Assignee: HydroCision, Inc., North Billerica, MA (US)

( * ) Notice: Subject to any disclaimer, the term of this patent is extended or adjusted under 35 U.S.C. 154(b) by 172 days.

(21) Appl. No.: 18/088,566

(22) Filed: Dec. 24, 2022

(65) Prior Publication Data
US 2023/0200840 A1 Jun. 29, 2023

Related U.S. Application Data

(60) Provisional application No. 63/293,714, filed on Dec. 24, 2021.

(51) Int. Cl.
*A61B 17/3203* (2006.01)
*A61B 17/00* (2006.01)
*A61B 17/22* (2006.01)
*A61B 17/221* (2006.01)
*A61M 25/00* (2006.01)
*A61M 25/01* (2006.01)

(52) U.S. Cl.
CPC ...... *A61B 17/32037* (2013.01); *A61B 17/221* (2013.01); *A61M 25/0097* (2013.01); *A61M 25/0147* (2013.01); *A61B 2017/00407* (2013.01); *A61B 2017/22038* (2013.01); *A61B 2017/22079* (2013.01); *A61B 2017/2215* (2013.01)

(58) Field of Classification Search
CPC ............ A61B 17/221; A61B 17/32037; A61B 2017/00323; A61B 2017/00407; A61B 2017/22038; A61B 2017/22079; A61B 2017/2215; A61B 2017/22082; A61M 25/0147; A61M 25/0097
USPC ......................................................... 606/159
See application file for complete search history.

(56) References Cited

U.S. PATENT DOCUMENTS

| | | | |
|---|---|---|---|
| 7,220,269 B1 * | 5/2007 | Ansel ............... | A61B 17/22032 604/35 |
| 9,655,633 B2 * | 5/2017 | Leynov .................. | A61B 17/22 |
| 2010/0286709 A1 * | 11/2010 | Diamant .......... | A61B 17/22022 606/128 |
| 2015/0112188 A1 * | 4/2015 | Stigall .................. | A61B 17/064 600/424 |
| 2021/0220006 A1 * | 7/2021 | Mitchell ........ | A61B 17/320758 |

* cited by examiner

*Primary Examiner* — Jocelin C Tanner
(74) *Attorney, Agent, or Firm* — Bochner PLLC; Andrew D Bochner; Eric R Kleinertz

(57) ABSTRACT

Provided is a medical device comprising a handle comprising a distal hub, a proximal hub, and a middle hub disposed between the distal hub and the proximal hub. The medical device may comprise an outer sheath coupled with the distal hub, a basket configurable in a deployed state and an undeployed state, and a jet tube shaft coupled with the proximal hub, the jet tube shaft coaxial to the outer sheath. The jet tube shaft may comprise a jet tube comprising an aperture configured to expel a fluid, a jet tube lumen sized to accept the jet tube, and an evacuation lumen.

17 Claims, 16 Drawing Sheets

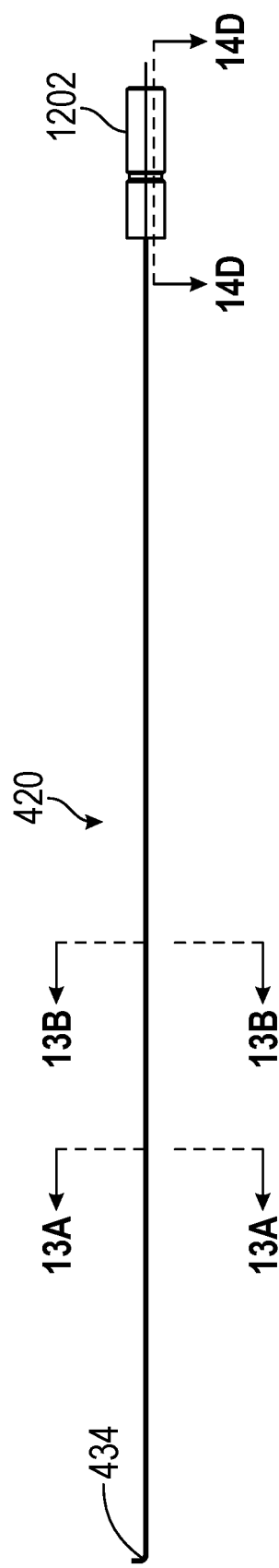
FIG. 12
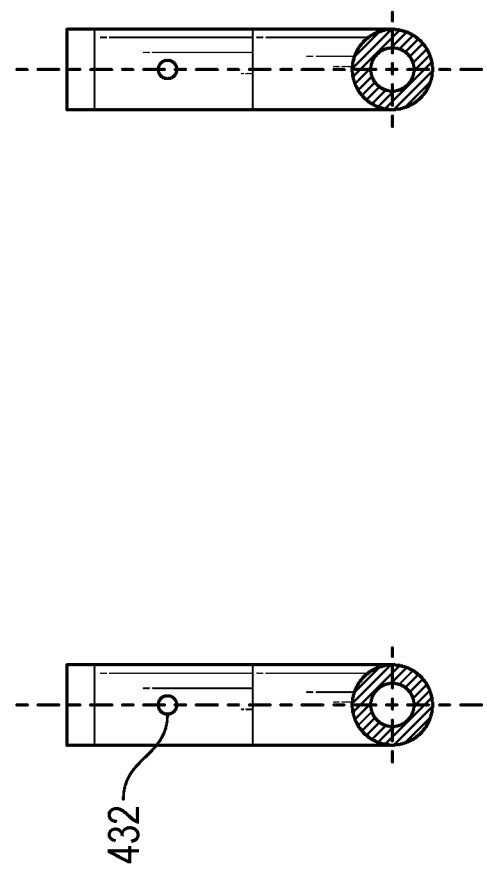
FIG. 13A
FIG. 13B

DEPLOYABLE DYNAMIC STENT AND ADJUSTABLE CUTTING JET DEVICE

FIELD OF THE INVENTION

The present disclosure relates to medical devices. More specifically, the present disclosure relates to stents and dynamic stents designed to protect and maintain vessel wall patency during deployment and activation.

INTRODUCTION

Thrombus formation, particularly in the iliofemoral, femoral, and popliteal veins can represent a significant clinical challenge once thrombus reaches the sub-acute and chronic stages of disease (for example, in patients diagnosed with venous thromboembolism [VTE]). Chronic clot formation, in particular, is defined as an unresolved clot or thrombus that has matured beyond 2 weeks of age. At this stage of disease progression, the thrombus' composition can be particularly dense, consisting of a combination of fibrin and collagen. In a thrombus' most severe, chronic form, it can become fibrotic scar tissue embedded within and along the walls of veins, arteries, or other vessels.

While a traditional stent may be used to maintain vessel patency, in thrombectomy a dynamic stent may be used as a receiver of thrombus. Thus, a traditional stent may have little utility in thrombus removal. However, it may be desirable to use a dynamic stent to shield a patient from the risk associated with cutting devices. It would therefore be desirable to provide a modified stent having a protective nature (for example, allowing the user to follow the treatment path and efficiently remove the stent from the patient).

Many commercially available thrombectomy devices may be configured to remove clots of acute nature. However, such thrombectomy devices may fail to adequately remove thrombus formation, especially once the condition reaches the chronic stage.

Waterjets (for example, high-powered waterjets) deployed through endovascular catheters may hold the potential of being aggressive enough to cut and evacuate chronic clot formation. However, such methods must be tailored as to preserve the delicate and elastic nature of vessel walls. Further, current thrombectomy devices may fail when removing chronic consistency and, especially, clots adhered to vessel walls. Moreover, catheters alone may be unsuitable as they utilize aspiration mechanisms, which may become overwhelmed and clogged in the presence of chronic thrombus.

In many instances, thrombectomy devices may be developed to 'reduce' aggressivity in order to provide protection. As a result, with such devices, physicians must generally submit patients to multiple procedures. Currently, the design of most thrombectomy devices renders them unable to remove thrombus of all types without supplementing with lytics, anticoagulants, and/or multiple sessions. The use of lytics combined with long in-dwelling sessions has been linked to vessel damage. Further, the combination of lytics and long in-dwelling sessions may cause other complications including, but not limited to, unacceptable blood loss and hemolysis. As a result, many traditional thrombectomy procedures may contribute to a relatively high cost of patient care per episode in addition to an increase in the frequency of potentially damaging invasive procedures.

In one particular instance, in the spine many procedures are rendered very complex in order to preserve the spinal dura. Many devices are too aggressive to provide maximum effectiveness while protecting the spinal dura.

It would be desirable to provide a dynamic stent capable of administering an effective jet, while protecting the vessel. It would further be desirable to provide the use of a deployable, expandable, stent being able to act as a scaffold or other protective mechanism while a fluidjet mechanism may be deployed inside a vessel at pressures high enough to enable the cutting and removal of thrombus of chronic consistencies.

SUMMARY

This Summary is provided to introduce a selection of concepts in a simplified form that are further described below in the Detailed Description. This Summary is not intended to identify key features or essential features, nor is it intended to limit the scope of the claims included herewith.

The invention of the present disclosure may be a dynamic stent device or, generally, a medical device. The medical device may comprise a handle comprising a distal hub, a proximal hub, and a middle hub disposed between the distal hub and the proximal hub. The medical device may further comprise an outer sheath coupled with the distal hub; a basket configurable in a deployed state and an undeployed state; and a jet tube shaft coupled with the proximal hub, wherein the jet tube shaft is coaxial to the outer sheath. The jet tube shaft may include a jet tube comprising an aperture configured to expel a fluid; a jet tube lumen sized to accept the jet tube; and an evacuation lumen.

In an embodiment, the distal hub is configured to translate movement of the distal hub to movement of the outer sheath. In a further embodiment, the proximal hub is configured to translate movement of the proximal hub to movement of the jet tube shaft.

The jet tube shaft may further comprise a guidewire lumen sized to accept a guidewire. In an embodiment, the jet tube lumen comprises a jet tube lumen cross-sectional area, the evacuation lumen comprises an evacuation lumen cross-sectional area, and the guidewire lumen comprises a guidewire lumen cross-sectional area, and the evacuation lumen cross-sectional area is greater than the guidewire lumen cross-sectional area, and the guidewire lumen cross-sectional area is greater than the jet tube lumen cross-sectional area.

In an embodiment, the handle further comprises a slider operably coupled to the jet tube, wherein the slider is configured to translate movement of the slider into movement of the jet tube. In a further embodiment, the jet tube comprises a bend orthogonal to the jet tube shaft, wherein the aperture is disposed on the bend, and wherein the aperture is configured to expel fluid toward the evacuation lumen. In yet a further embodiment, the bend is disposed proximal to a leading edge of the basket. The basket may be composed of nitinol.

In an embodiment, the handle further comprises a ratchet coupled to one or more pull wires, wherein the one or more pull wires are coupled to a distal end of the outer sheath, and wherein actuation of the ratchet induces deflection in the distal end of the outer sheath via the one or more pull wires. The outer sheath may further comprise one or more pull wire channels disposed in a sidewall of the outer sheath, wherein the one or more pulls wire channels are sized to accept each of the one or more pull wires.

In an embodiment, the basket is a mesh structure. In a further embodiment, in the undeployed state, the basket is configured to conform to the outer sheath, and, in the deployed state, the basket is configured to radially expand. The basket may further comprise a leading edge, wherein, in the deployed state, the leading edge is concave, and wherein, in the deployed state, the basket is conical. Further, the basket may include one or more markers, wherein the markers are configured to be radiopaque in fluoroscopy and radiography. In an embodiment, the jet tube comprises a bevel disposed on a distal end of the jet tube.

In an embodiment, the invention of the present disclosure is a medical device comprising a dynamic stent having a proximal stent end, a distal stent end, a distal stent circumference, and a proximal stent circumference, where the dynamic stent is composed of a mesh, and where the mesh is composed of a material. The device may further comprise a passive state and an active state, where, in the passive state, the distal stent circumference is equivalent to the proximal stent circumference, and where, in the active state, the distal stent circumference is greater than the proximal stent circumference. Further, the device may include a jet at least partially disposed within the dynamic stent, the jet configured to divorce a thrombus, and a cylindrical hollow member attached to the proximal stent end, where the cylindrical hollow member at least partially encompasses the jet. The material may be nitinol.

BRIEF DESCRIPTION OF THE DRAWINGS

The drawings should, in no way, be construed as limitations on embodiments of the disclosed invention. Objects, aspects, features, and advantages of embodiments disclosed herein will become more fully apparent from the following detailed description, the appended claims, and the accompanying drawing figures in which like reference numerals identify similar or identical elements. Reference numerals that are introduced in the specification in association with a drawing figure may be repeated in one or more subsequent figures without additional description in the specification in order to provide context for other features, and not every element may be labeled in every figure. The drawing figures are not necessarily to scale, emphasis instead being placed upon illustrating embodiments, principles and concepts. The drawings are not intended to limit the scope of the claims included herewith.

FIG. 12 illustrates an embodiment of the jet tube.

FIGS. 13A-13B illustrate cross-sectional views of an embodiment of the jet tube.

Figure 1A:
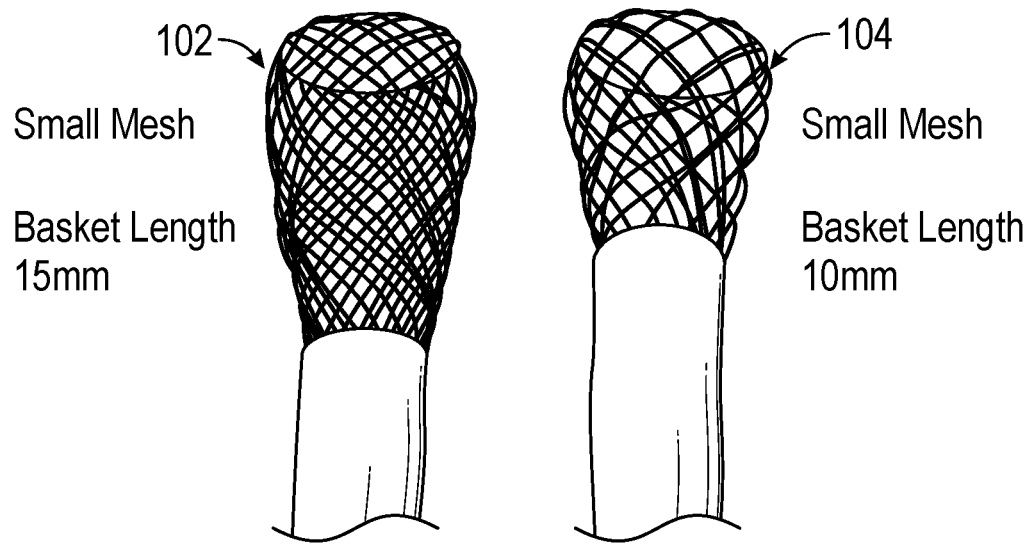
FIGS. 1A-1B illustrate embodiments of dynamic stents.

| Parts List | |
|---|---|
| 100 | dynamic stent |
| 102 | small mesh |
| 104 | large mesh |
| 400 | handle |
| 402 | outer sheath |
| 404 | closed position |
| 406 | acute/subacute position |
| 408 | extended position |
| 410 | distal hub |
| 412 | middle hub |
| 414 | proximal hub |
| 416 | basket |
| 418 | basket shaft |
| 420 | jet tube |
| 422 | jet tube shaft |
| 424 | jet lumen |
| 426 | guidewire lumen |
| 428 | evacuation lumen |
| 430 | ratchet pull handle |
| 432 | aperture |
| 434 | bend |
| 436 | marker |
| 438 | slider |
| 440 | guidewire access |
| 502 | pull wire |
| 504 | pull wire channel |
| 602 | enhanced extended position |
| 1202 | LC filter |
| 1204 | filter media |
| 1206 | spacer tube |
| 1208 | first portion |
| 1210 | second portion |
| 1212 | indentation |

DETAILED DESCRIPTION

For this disclosure, singular words should be construed to include their plural meaning, unless explicitly stated otherwise. Additionally, the term "including" is not limiting. Further, "or" is equivalent to "and/or," unless explicitly stated otherwise. Although, ranges may be stated as preferred, unless stated explicitly, there may exist embodiments that operate outside of preferred ranges.

In the following detailed description, reference will be made to the accompanying drawing(s), in which identical functional elements are designated with like numerals. The aforementioned accompanying drawings show by way of illustration, and not by way of limitation, specific aspects, and implementations consistent with principles of this disclosure. These implementations are described in sufficient detail to enable those skilled in the art to practice the disclosure and it is to be understood that other implementations may be utilized and that structural changes and/or substitutions of various elements may be made without departing from the scope and spirit of this disclosure. The following detailed description is, therefore, not to be construed in a limited sense.

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

The invention of the present disclosure may be a dynamic stent for use in venous, arterial, spinal, or other suitable applications. The dynamic stent may be utilized in conjunction with a jet that is aggressive to tissue. Thus, the dynamic stent may provide a useful means of protection in confined spaces having sensitive structures. In one embodiment, the dynamic stent may be utilized in protecting spinal nerves.

In an embodiment, the dynamic stent may be configured for use with sensitive structures such as nerves, arteries, or other healthy soft tissues. In an instance where a vessel has uneven sides, the stent and jet may be configured to provide 'directional' protection, for example, in a biplane area where one plane must be resected while the other must be left intact. As a non-limiting example, such instances may exist where a nerve traverses the space or where a fat pad must be separated from muscle without harming the latter.

The invention of the present disclosure may be a dynamic stent. In an embodiment, the dynamic stent design may enable an outer sheath (for example, composed of nylon or other suitable materials) to close the stent for deployment and retrieval purposes. For the purposes of this disclosure, the term "dynamic" may be utilized to describe the fact that the stent may not be left in a patient's body. Instead, "dynamic" may be utilized to describe the fact that the stent is deposited and withdrawn from the patient over the course of a procedure. However, in an alternate embodiment, the stent as described in this disclosure may be utilized in procedures of any suitable duration. For the purposes of this disclosure, the terms "jet," "fluidjet," and "waterjet" may refer to a component configured to remove tissue via suction, cutting, pressure, and/or other means. Further, in an embodiment, the jet and the stent may be integrated, such that the stent and jet are a single construct. In a further embodiment, the jet and the stent (or "basket") may be operably connected such that either component is moveable relative to the other component, while permitting simultaneous utilization.

In an embodiment, the jet, while operating at various power settings, may elicit the need for protection to the patient's vessels. In such an embodiment, the dynamic stent may be a beneficial component in enabling direct thrombus exposure to the jet and resulting venturi effect. The resulting venturi effect may create a low pressure zone. Such an effect may enable one of the jet's primary functions, cutting. In an embodiment, the pressurized fluid jet resects even chronic thrombus when presented to the stream of fluid (i.e., saline). While the jet draws in and severs unwanted tissue, as a side effect an unprotected jet may pull the vein as well. Thus, in an embodiment, the dynamic stent is configured to prevent this from happening by maintaining a wider diameter around the jet area.

Referring to FIG. 1A, the apparatus may include a dynamic stent. The stent may be composed of mesh. In various embodiments, the mesh may be of variable lengths and widths in order to conform to the vessel wall diameters of the deep veins of the legs as well as arteries once in open form. The length and width may be determined by the inner diameter of the vessels, as a function of the dynamic stent may be to create a temporary scaffold during jet operation. The mesh may have a wider weave and as such be more open or transparent, for example, the large mesh 104 as shown on the right side of FIG. 1A. In an embodiment, the mesh may have a proximal end and a distal end, where the distal end is configured to make initial contact with a thrombus. In various embodiments, the stent may be of any suitable length. The stent may be longer, for example, the 15 mm large stent 104 as shown in FIG. 1A. The stent may be shorter, for example, the 10 mm small stent 102 as shown in FIG. 1A. However, in various embodiments, the stent may be any suitable length. The stent may incorporate concave angled distal edges to allow it to conform and track along vessel walls upon advancement. Further, such concave angled distal edges may prevent the stent from negatively snagging a vessel wall.

Figure 1B:
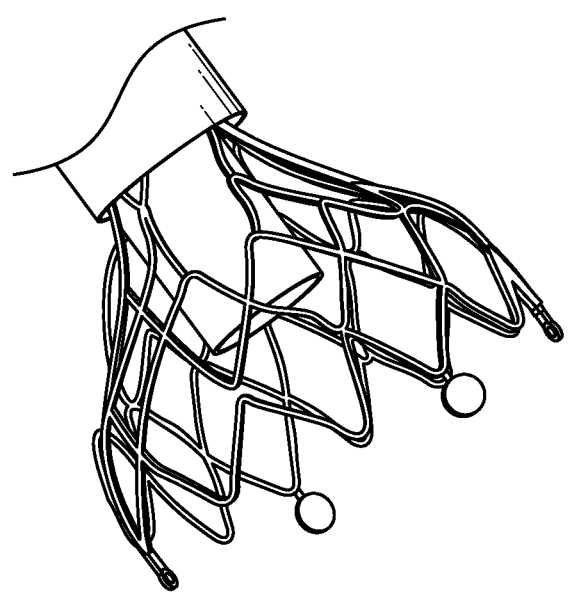

In an embodiment, the catheter may be a 12 F catheter with an integrated expandable nitinol cage capable of expanding to conform to the inner diameter of the deep veins. Accordingly, an outer nylon sheath may allow for stent deployment. Referring to FIG. 1B, the cage may be capable of "bowing open" and encompassing clot formation with forward advancement. In such an embodiment, the distal leading edges of the design are slightly concave in order to minimize vessel wall trauma. Further, the leading edges of the stent may be coated, filed, or otherwise rendered smooth to decrease the sharpness of said leading edges. In an embodiment, the invention of the present disclosure may incorporate the fluidjet such that it is mounted within its own lumen. The fluidjet may have the ability to be pistoned forward by the operator proximally within predefined limits.

The dynamic stent and accompanying fluidjet may be configured to be venous compliant and/or arterial compliant. Accordingly, the dynamic stent and accompanying fluidjet may impart no damage to the veins and/or arteries. In an embodiment, sub-acute thrombus is taken first, followed by chronic thrombus (for example, having a thicker consistency). A telescoping fluidjet and/or telescoping stent, the ability of the stent to encompass the thrombus during an antegrade technique, and simultaneous advancement of the fluidjet aids in chronic thrombus removal.

In an embodiment, the mesh stent tapers from the distal end to the proximal end. The distal end of the mesh stent may include a circular opening of a distal circumference. The opening at the distal circumference may have edges that are smooth and tapered inward. In an embodiment, a coating may be applied to the mesh stent (for example, to the distal circumference), where the coating is configured to reduce friction. The mesh stent may widen slightly to a bow circumference and finally taper to a proximal circumference at the proximal end of the mesh stent. However, in another embodiment, the circumference of the mesh stent may decrease uniformly from the distal end to the proximal end. The bow circumference may define the widest portion of the stent in an embodiment where the stent is not uniformly tapered. Further, the aforementioned circumferences may be variable and fluctuating. For example, the aforementioned circumferences may fluctuate as the stent is deployed or withdrawn. However, in an alternate embodiment, the stent may be relatively rigid and the aforementioned circumferences may only negligibly fluctuate.

The proximal end of the mesh stent may be attached to a catheter. The catheter may have a distal end and a proximal end. The proximal end of the mesh stent may contact the distal end of the catheter. The catheter may also house the fluidjet, lumens, or other members configured to remove or introduce material to the vessel. The catheter and/or the outer jacket/sheath may be transparent.

In an embodiment, the catheter and the mesh stent are fastened via an adhesive. However, in alternate embodiments, the catheter and the mesh stent may be fastened via any suitable means. In an embodiment, the catheter is a two-lumen catheter (for example, am first lumen sized for the jet and a second lumen configured for evacuation). In an embodiment, the stent may be fastened via the distal outer wall of the catheter. In an alternate embodiment, the stent may be attached to the inner wall of the catheter.

In an embodiment, the outer distal edges of the dynamic stent are atraumatic (for example, allowing for safe passage and navigation within the vessel once deployed). The outer jacket/sheath may enable the operator to unsheathe and open the stent to form a conical shape. The outer jacket/sheath may be composed of nylon or any other suitable material. The outer jacket may be a long cylindrical hollow member configured to removably encapsulate at least the dynamic stent. However, the outer jacket may be any suitable shape, length, or thickness. The outer jacket may be configured such that a user may manipulate the outer jacket to remove it from the distal end of the stent. In another embodiment, the dynamic stent operates without the outer jacket.

Figure 2A:
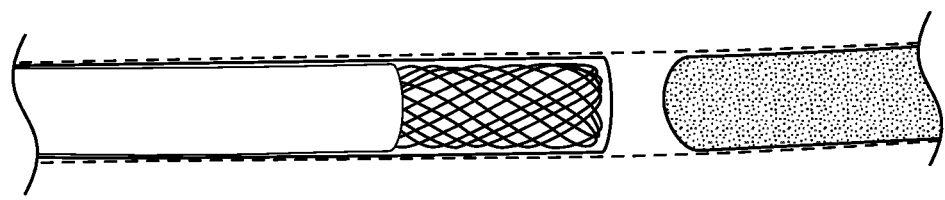
FIGS. 2A-2B illustrate embodiments of the dynamic stents with an outer jacket/sheath, before and after deployment.
Figure 2B:
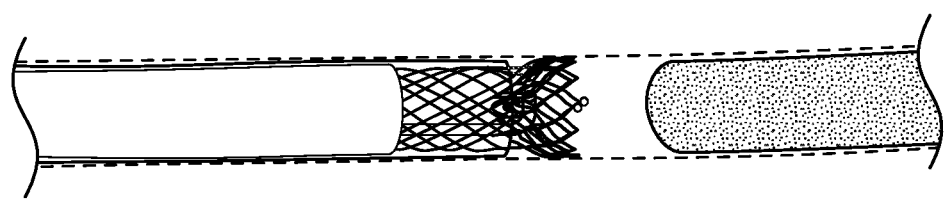

FIG. 2A depicts an embodiment of the dynamic stent as it is partially enclosed by an outer jacket/sheath. In such an embodiment, the dynamic stent may adhere to the internal cross-sectional circumference of the outer jacket/sheath. FIG. 2B depicts an embodiment of the dynamic stent where the outer jacket/sheath is retracted. In such an embodiment, the distal edges of the stent may adhere to the internal cross-sectional circumference of the vessel. As a non-limiting example, the dynamic stent may form a generally conical shape. However, in alternate embodiments, the dynamic stent may be designed such that the dynamic stent is any shape, with or without the constriction of the outer jacket/sheath.

For the purposes of this disclosure, FIG. 2A may be representative of a passive state and FIG. 2B may be representative of an active state. The active state may be actuated by partial or complete retraction of the outer jacket/sheath. Similarly, the dynamic stent may return to the passive state, from the active state, by partially or completely reapplying the outer jacket/sheath.

The dynamic stent may be composed of nitinol or any other suitable material (for example, stainless steel). The use of nitinol may allow the dynamic stent to maintain its intended form and function once deployed. In an embodiment, a suitable material may exhibit a combination of strength, flexibility, and atraumatic properties to be able to deploy, move, and maintain a vessel open under negative pressure. The conical shape and side-wall mesh design may allow the dynamic stent to conform to venous vessel wall structures (or any other suitable vessel). Such a conical shape may aid in preventing blood from being suctioned from behind and/or proximal to the fluidjet. However, in various alternate embodiments said dynamic stent shape may be configured such that thrombus in front of, surrounding, and/or behind the mesh is removed. In an embodiment, the dynamic stent has a sufficient plasticity enabling the stent to conform to the dimensions of the vessel and return to its pre-deployed shape.

The deployabilty of the stent may allow simpler navigation and selective protection. As a non-limiting example, if a portion of a vessel was already stented, the dynamic stent may be retracted to allow the open jet to penetrate the clot material and resect it efficiently.

Once properly positioned in an antegrade fashion proximal to the clot, the fluidjet may be safely centered within the dynamic stent. In various embodiments the fluidjet may be positioned in any manner that suitably enables the removal of thrombus. For example, along a straight portion of vessel, the fluidjet may be relatively centered about the stent. Further, as a non-limiting example, along a curved portion of vessel, the fluidjet may be positioned along any of the sides of the stent. In an embodiment, the fluidjet position is fixed. In another embodiment, the fluidjet position may be manipulated by a user (for example, the user may insert, withdraw, rotate, and/or otherwise move the fluidjet from outside the patient). In an embodiment where the fluidjet is fixed within the catheter, the fluidjet may be centered in the vessel relative to the vessel circumference. However, in another embodiment, the fluidjet may be fixed, such that the fluidjet is centered within the stent, but may be longitudinally telescoped (for example, in parallel with the catheter or along the longitudinal axis of the catheter). In such a telescoping embodiment, the fluidjet may have predefined limits (for example, proximal, mid-point, at distal edge, and extension outside distally).

The fluidjet may be activated at pressures as high as 15,000 psi without compromising the integrity of vessel walls, which may otherwise potentially encroach onto the fluidjet due to suction forces exerted by the fluidjet system. Such use without the dynamic stent could increase the potential for vessel injury and damage. The protection offered by the dynamic stent may enable the fluidjet system to operate at a velocity and pressure sufficiently high enough to remove chronic clot consistencies. However, the pressure exerted by the fluidjet may be any pressure capable of removing thrombus.

Figure 3A:
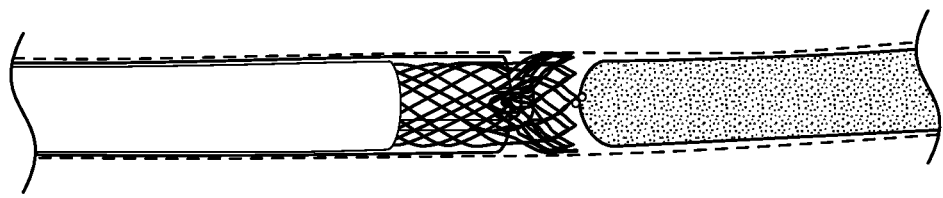
FIGS. 3A-3C illustrate an embodiment of the dynamic stent and jet in contact with a thrombus.
Figure 3B:
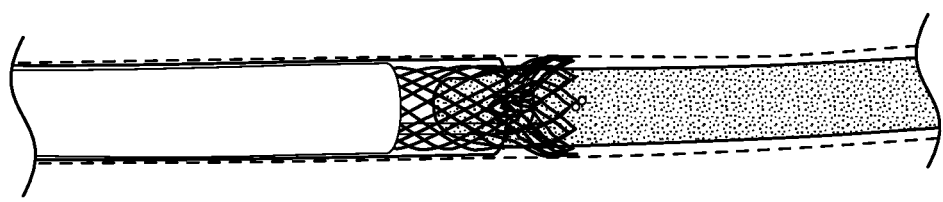
Figure 3C:
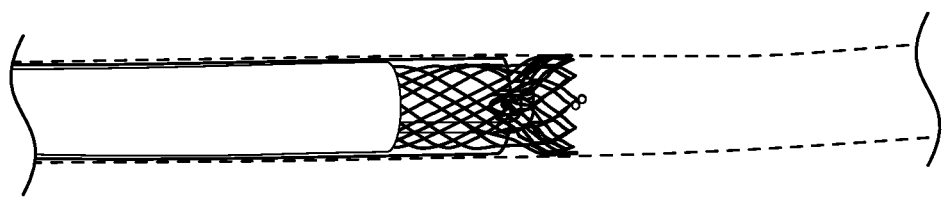

FIG. 3A depicts an embodiment of the dynamic stent where the stent has made initial contact with a thrombus. FIG. 3B depicts an embodiment of the dynamic stent where a majority of the thrombus has been vacuumed into the mesh. FIG. 3C depicts an embodiment of the dynamic stent where the thrombus has been successfully cleared from the vessel and the mesh.

In an embodiment, it may be desirable to prevent ingress of tissue from behind the cutting tip. In such an embodiment, a tight weave or a complete shielding (for example, an additional sheath) may be desirable. As a non-limiting example, a sheath may be utilized instead of a mesh.

The atraumatic, distal edges of the dynamic stent may be spring-tensioned to allow for extension and/or telescoping of the fluidjet (for example, when the dynamic stent encounters dense material). The spring tension may be a function of both the material and structure of the stent. In an embodiment, the fluidjet is positioned within a fluidjet-dedicated lumen, such that the fluidjet is centered and can be extended within predefined limits in relation to the distal end of the stent. Accordingly, the operator may be able to control the fluidjet proximally. In an embodiment, when the system encounters resistance consistent with chronic clot formation, the outer edges of the stent will spring backwards in a retrograde fashion, exposing the fluidjet more fully to the chronic clot formation. Conversely, in an embodiment, when the leading edges of the stent encounter little or no resistance, the fluidjet device will be maintained in the center of the stent construct. In such an embodiment, this feature may allow for passive removal of thrombus material of acute, subacute, and chronic consistency. In another embodiment, the user may manually select the position of the fluidjet in relation to the dynamic stent. For example, the user may manually insert or withdraw the fluidjet relative to the stent and/or thrombus.

In an embodiment, the fluidjet and/or dynamic stent may be introduced to a vessel with the assistance of a guide wire. A guide wire may be used in instances where the fluidjet and/or dynamic stent must be passed through a seal. In an embodiment, the guidewire may be deployed through the evacuation lumen. However, in another embodiment, the guidewire may be deployed through a dedicated guidewire lumen. There exist embodiments where the dynamic stent may be introduced to the vessel with or without the assistance of a guidewire.

In an embodiment, the dynamic stent may be used with any suitable medical equipment. As non-limiting examples, the dynamic stent may be configured for use with medical grade pumps, fluidjets, lumens, vacuums, catheters, etc.

For the purposes of this disclosure, "dynamic stent," "stent," and "basket" may be used interchangeably. Further, "fluidjet" and "jet" may be used interchangeably. Moreover, the dynamic stent device 100 may refer to a device comprising a basket and a jet, or aspects of either a basket and a jet.

Figure 4A:
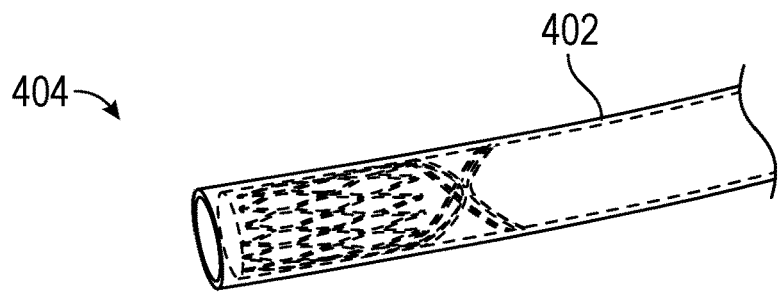
FIGS. 4A-4B illustrate an embodiment of the dynamic stent device in a closed position.
Figure 4B:
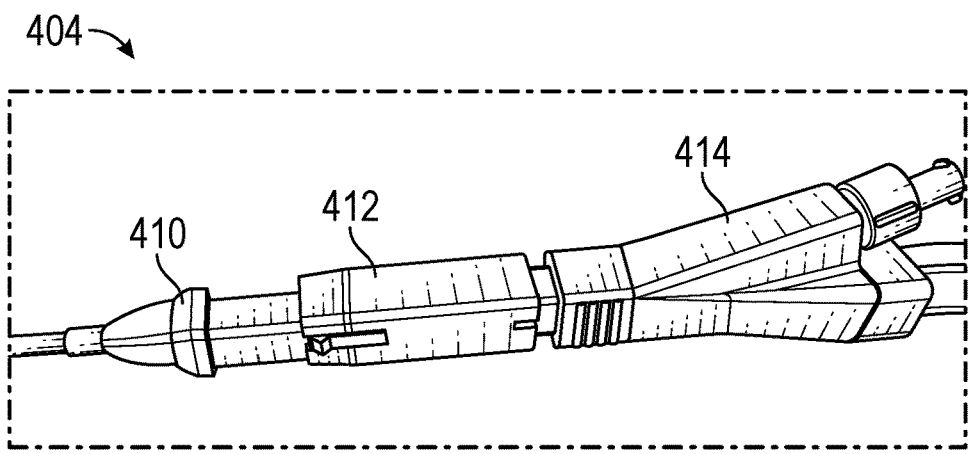

FIGS. 4A-4B illustrate an embodiment of the dynamic stent device 100 in a closed position 404. The dynamic stent device 100 may include a handle 400. In an embodiment, the handle 400 may be sized to be grasped by an operator and/or may include various inputs and outputs adapted to enable or supplement the functions described herein. The handle 400 may be manipulated as to induce various actions. For example, the handle 400 may be manipulated as to sheath and unsheathe the basket 416 and/or extend the jet tube shaft 422. The handle 400 may comprise a plurality of hubs. As a non-limiting example, the handle 400 may include a proximal hub 414, a middle hub 412, and a distal hub 410. In an embodiment, the movement of each of the hubs relative to the other hubs may induce one of the aforementioned actions. As shown in FIGS. 4A-4B, the distal hub 410 may be operably separated from the middle hub 412 and the middle hub 412 may be operably separated from the proximal hub 414, to place the dynamic stent device 100 in a closed position 404. In a closed position 404, the basket 416 may be sheathed within the outer sheath 402.

Figure 4C:
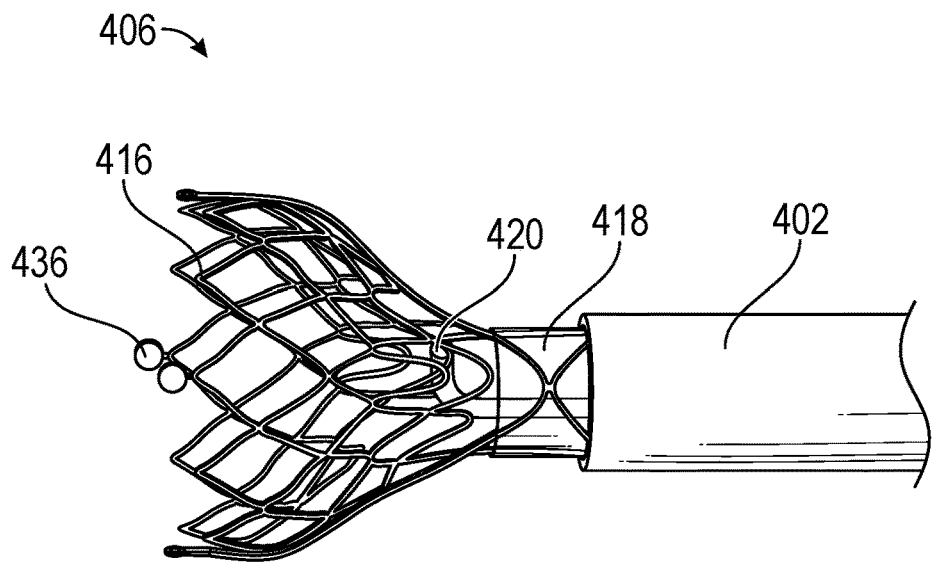
FIGS. 4C-4D illustrate an embodiment of the dynamic stent device in an acute/subacute position.
Figure 4D:
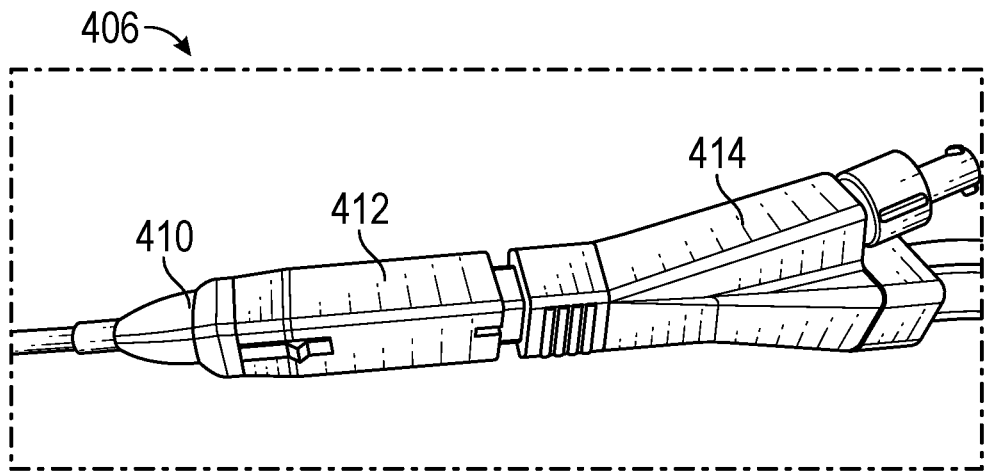

FIGS. 4C-4D illustrate an embodiment of the dynamic stent device 100 in an acute/subacute position 406. In an acute/subacute position 406 the basket 416 may be in a deployed configuration. For example, the outer sheath 402 may be retracted, such that the basket 416 and/or jet tube 420 are distally protruding relative to the outer sheath 402. In such an embodiment, the distal ends of the basket 416 and the jet tube 420 may be flush. In one embodiment, the dynamic stent device 100 may be converted to the acute/subacute position 406 when the distal hub 410 is operably interfaced with the middle hub 412 and the middle hub 412 is operably separated from the proximal hub 414. In the acute/subacute position 406, the dynamic stent device 100 may be a more aggressive means of removing a clot, for example, relative to when the venturi effect may be utilized entirely within the confines of a lumen. Therefore, by protruding the jet tube 420 and basket 416 distally, as shown in FIG. 4C, the dynamic stent device 100 may more aggressively remove debris while mitigating harm to the surrounding vessel.

Figure 4E:
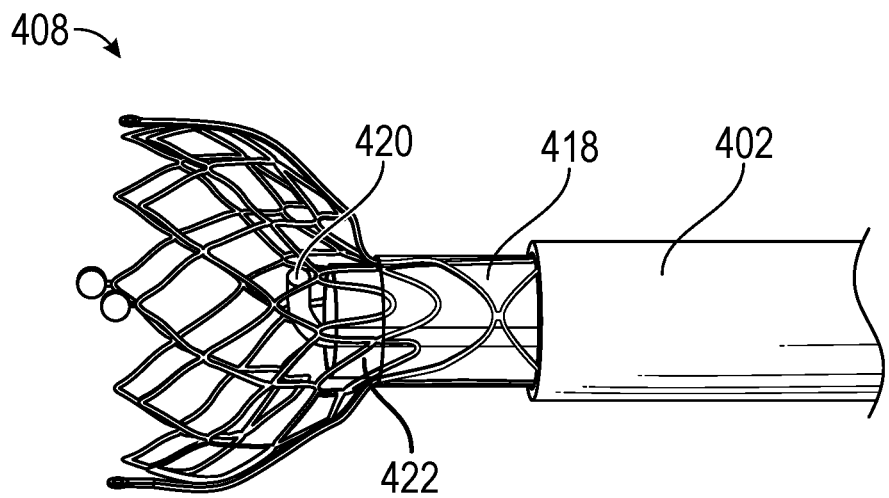
FIGS. 4E-4F illustrate an embodiment of the dynamic stent device in an extended position.
Figure 4F:
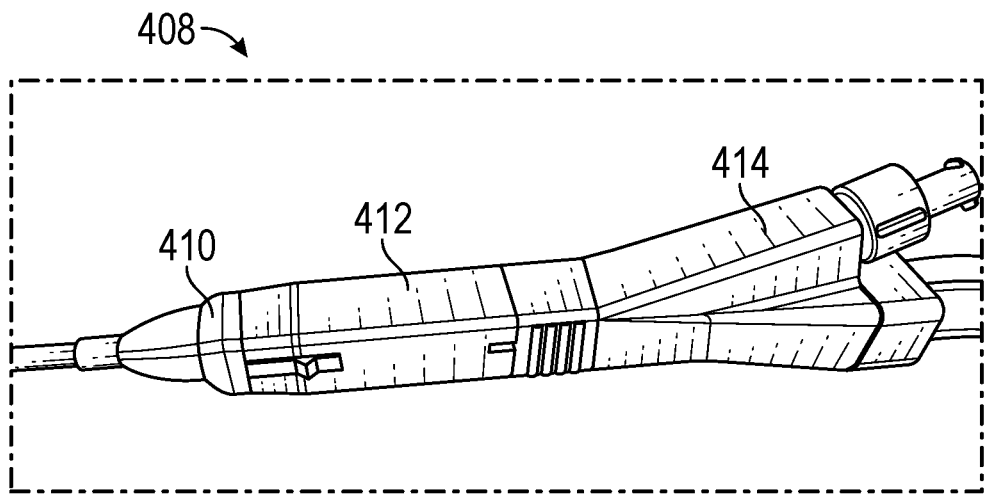

FIGS. 4E-4F illustrate an embodiment of the dynamic stent device 100 in an extended position 408. In an extended position 408, the jet tube 420 may be extended distally relative to the basket shaft 418 and/or outer sheath 402. In one embodiment, the dynamic stent device 100 may be converted to the extended position 408 when the distal hub 410 is operably coupled to the middle hub 412 and the middle hub 412 is operably coupled to the proximal hub 414. The extended position 408 may be configured for removal of chronic clot formation, for example, allowing the bend 434 of the jet tube 420 to more aggressively enter such a chronic clot. However, in the extended position 408, the jet tube 420 may remain within the volume of the deployed basket 416. In an embodiment, in the extended position 408, the jet tube 420 and/or the jet tube shaft 422 may protrude distally past the most distal portion of the basket shaft 418. For example, in the acute/subacute 406 position, the jet tube shaft 422 may be flush with the basket shaft 418 (not including the basket 416 itself). Further, in such a non-limiting example, in an extended position 408, the jet tube shaft 422 may extend distally past the basket shaft 418 (not including the basket 416 itself).

Figure 5A:
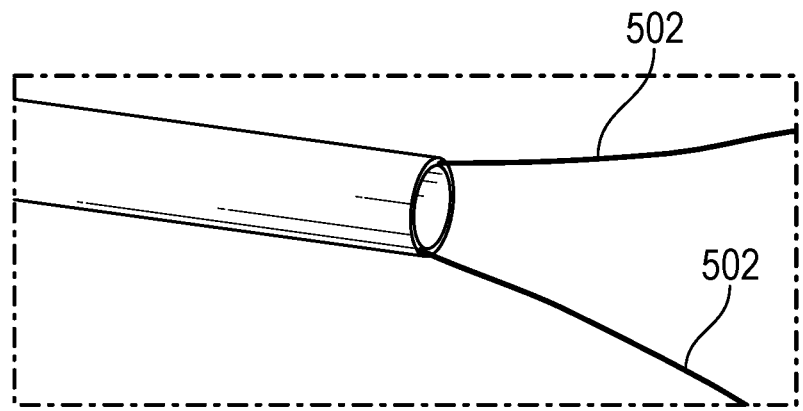
FIGS. 5A-5B illustrate an embodiment of the dynamic stent device comprising pull wires.
Figure 5B:
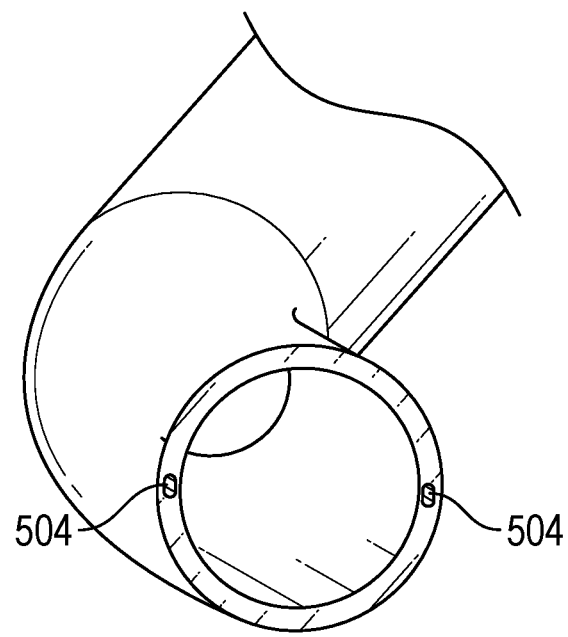

FIGS. 5A-5B illustrate an embodiment of the dynamic stent device 100 comprising pull wires 502. In an embodiment, one or more pull wires 502 may be disposed within the outer sheath 402. In such an embodiment, the one or more pull wires 502 may be housed within pull wire channels 504 disposed in the wall of the outer sheath 402. As a non-limiting example, the dynamic stent device 100 comprises two pull wires 502, wherein each pull wire 502 is disposed on opposite sides of the outer sheath 402 wall. Accordingly, inducing tension in one or more of the pull wires 502 may cause the corresponding portion of the outer sheath 402 to bend in the corresponding direction. The deflection capability as induced by the pull wires 502 may allow the dynamic stent device 100 to capture and/or remove a total clot circumference and/or allow for rotational sweeping of vessel walls. Further yet, the one or more pull wires 502 may be coupled with handle 400 controls such that actuation of said handle 400 controls may induce distal end deflection. For example, the handle 400 may include a ratchet pull handle 430 configured to actuate at least one of the one or more pull wires 502.

Figure 6A:
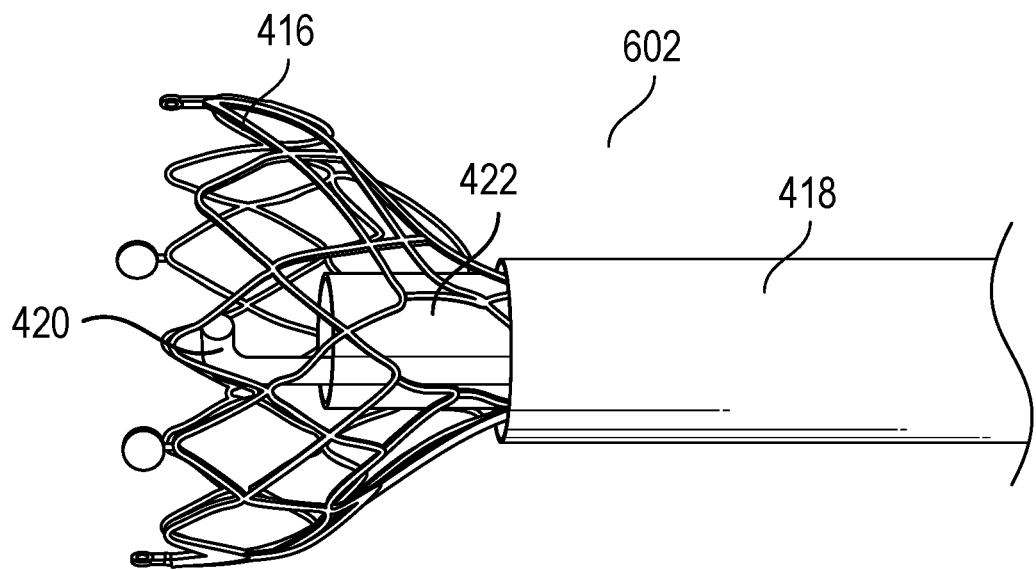
FIGS. 6A-6B illustrate an embodiment of the dynamic stent device in an enhanced extended position.
Figure 6B:
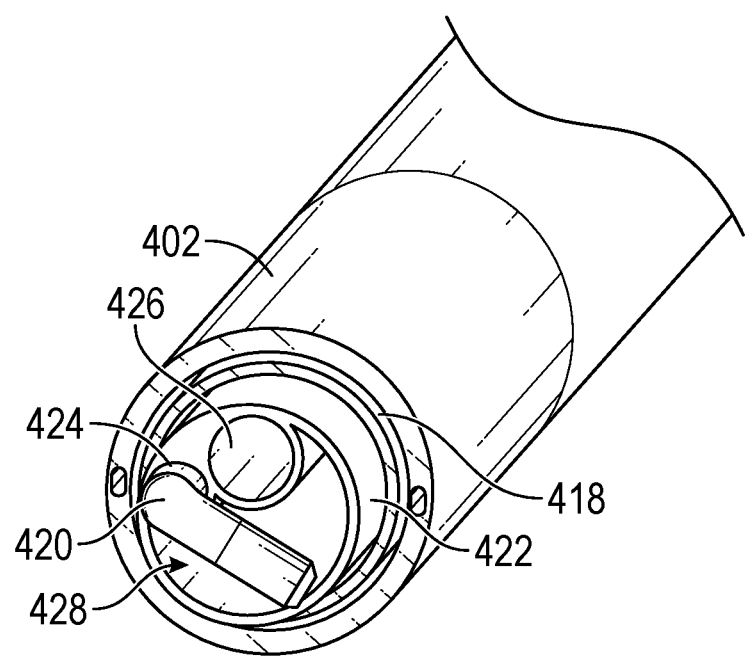

FIGS. 6A-6B illustrate an embodiment of the dynamic stent device 100 in an enhanced extended position 602. The enhanced extended position 602 may be configured for increased aggressivity for chronic clot formation. In such an embodiment, the bend 434 may be extended distally in relation to evacuation lumen 428. For example, the bend 434 may be extended up to an additional 3 mm. However, the bend 434 may be extended any suitable distance in the enhanced extended position 602. In an embodiment, radiopaque markers 436 may be disposed on the distal edge (also referred to as the "leading edges") of the basket 416. However, radiopaque markers 436 may be disposed on any suitable portion of the dynamic stent device 100. Thus, the radiopaque markers 436 may increase the dynamic stent device 100 visibility via fluoroscopy, radiography, or other related imaging technologies.

In an alternate embodiment, the jet tube 420 may be configured to expel fluid in a direction perpendicular to the vessel wall. For example, the aperture 432 may be disposed facing the vessel wall. In such an alternate embodiment, a flat surface, lumen, or partial lumen may be disposed opposite the aperture 432, such that the fluid and cut thrombus is captured and removed.

In another alternate embodiment, an evacuation lumen 428 may be disposed distal to the jet tube 420. In such an embodiment, the jet tube 420 may expel fluid distally or partially distally, such that the evacuation lumen 428 initiates first contact with a clot or other undesired material.

In yet another alternate embodiment, the jet tube 420 may be replaced with a source of suction instead of a source of pressurized fluid.

Figure 7:
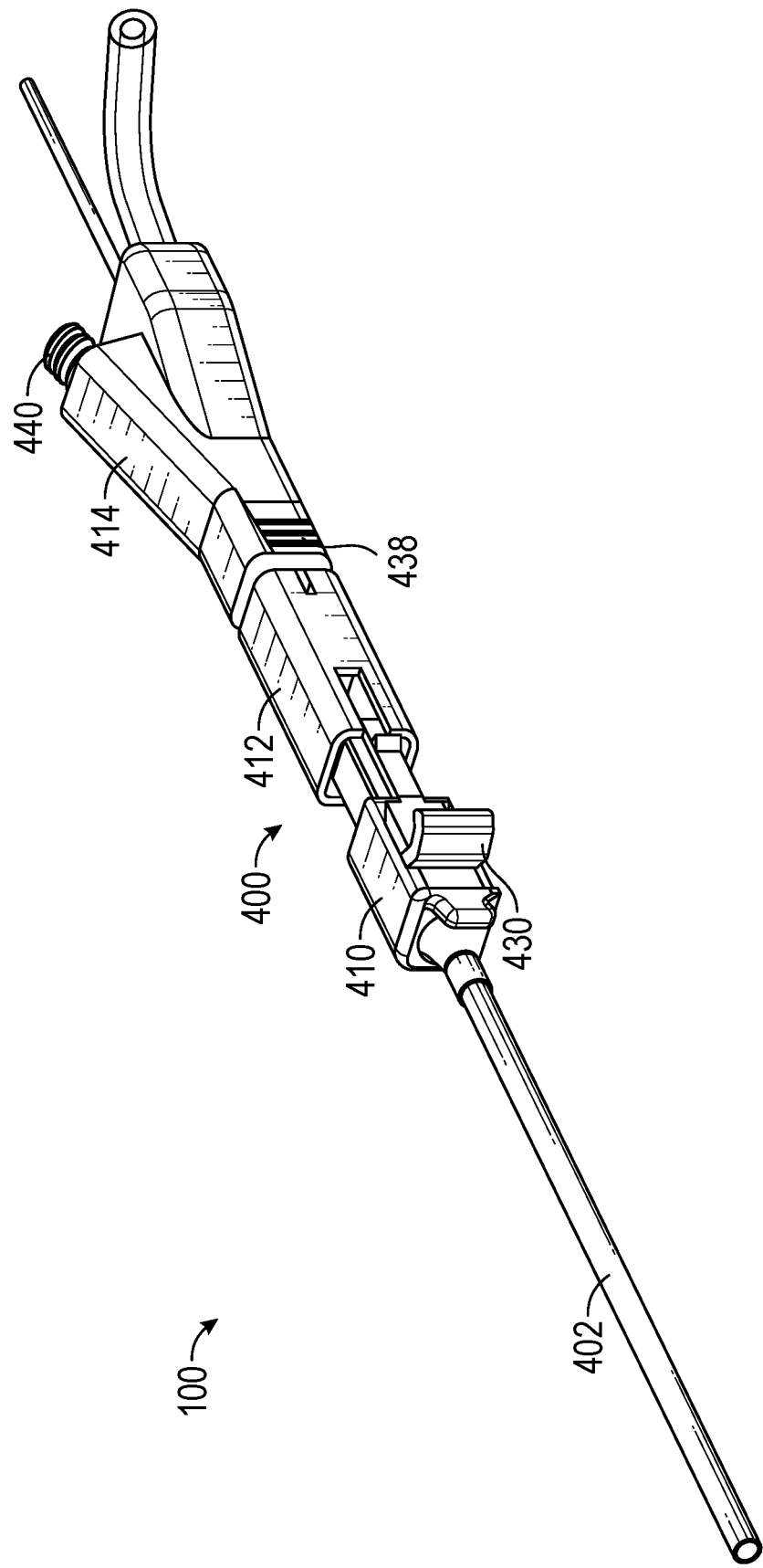
FIG. 7 illustrates an embodiment of the dynamic stent device in a closed position.

FIG. 7 illustrates an embodiment of the dynamic stent device 100 in a closed position 404. Thus, the distal hub 410, the middle hub 412, and the proximal hub 414 may be each be operably separated.

The handle 400 may include a slider 438. The slider 438 may be operably connected to the jet tube 420, such that actuation of the slider 438 distally pushes the jet tube 420. For example, the slider 438 may be utilized to convert the dynamic stent device 100 to the enhanced extended position 602. The enhanced extended position 602 may be configured for removal of particularly aggressive thrombus. In effect, by projecting the jet tube 420 distally the jet tube 420 may more aggressively remove the thrombus. In an embodiment, the slider 438 may be adapted to push the jet tube 420 distally relative to the degree of motion of the slider 438. For example, half-way actuation of the slider 438 may push the jet tube 420 distally half-way of its potential travel distance. However, the slider 438 may also be configured with binary actuation. For example, the slider 438 may comprise two states: an actuated state wherein the slider 438 is pushed forward to convert the jet tube 420 to an enhanced extended position 602; and an unactuated state wherein the slider 438 is unmoved. Thus, the slider 438 may be configured to induce movement in the jet tube 420 relative to the degree of motion in the slider 438; or the slider 438 may be configured to select between two absolute positions, such as the extended position 408 and the enhanced extended position 602. Although a "slider" is provided in FIG. 7 to demonstrate the slider 438, the slider 438 may be any suitable means of actuation, including, but not limited to, a switch, a lever, a button, or the like.

In an embodiment, the handle 400 may include a guidewire access 440 disposed near the proximal end of the handle 400. The guidewire access 440 may include an entrance enabling access to the guidewire lumen 426.

Figure 8A:
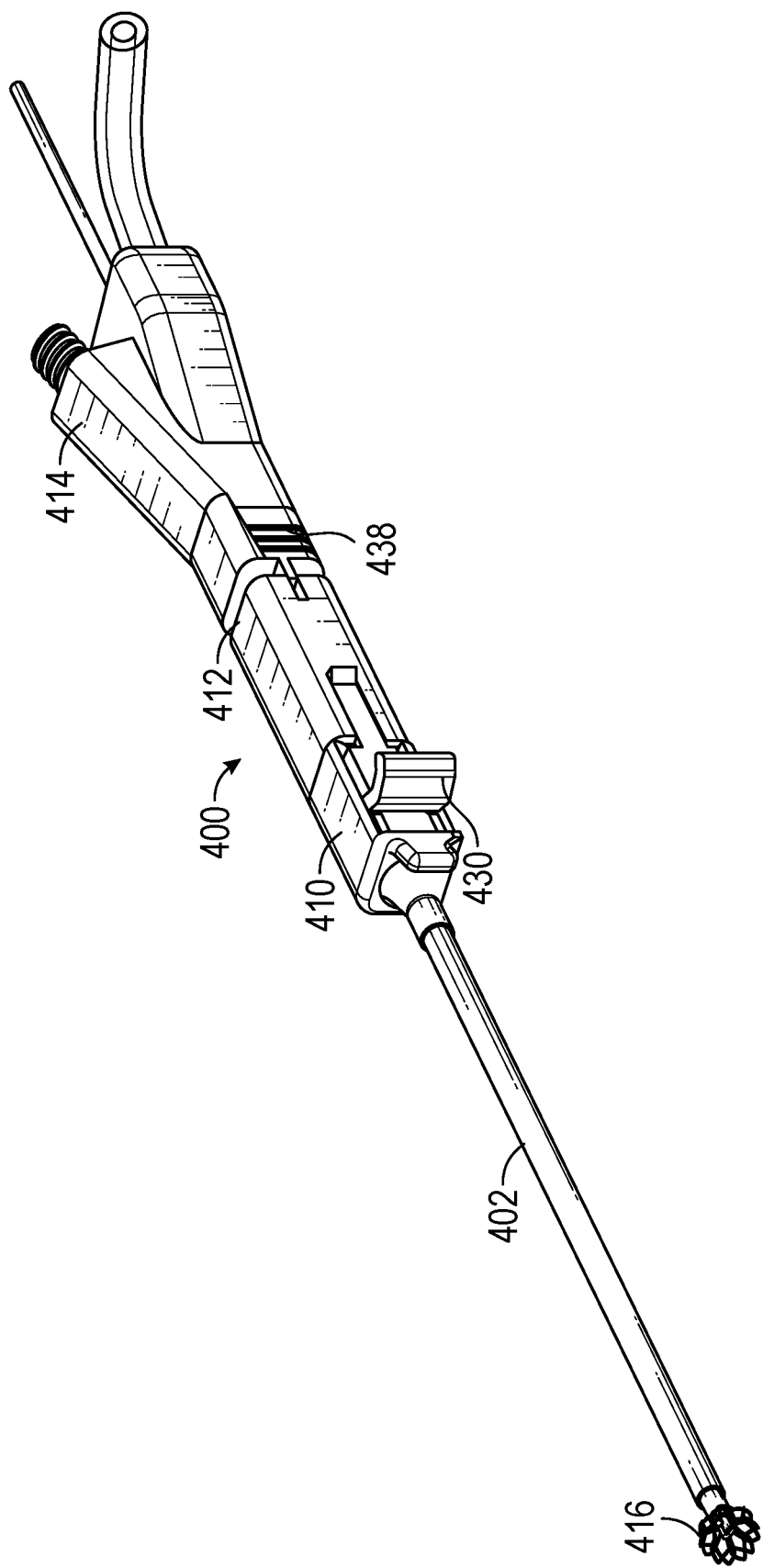
FIGS. 8A-8B illustrate an embodiment of the dynamic stent device in an acute/subacute position, wherein the outer sheath may be retracted, exposing the basket.
Figure 8B:
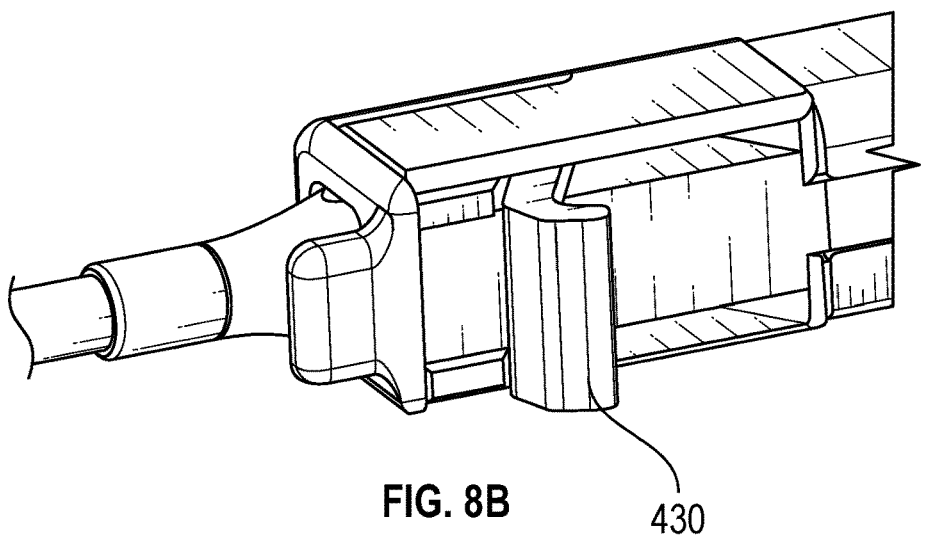

FIGS. 8A-8B illustrate an embodiment of the dynamic stent device 100 in an acute/subacute position 406, wherein the outer sheath 402 may be retracted, exposing the basket 416. Thus, the distal hub 410 may be operably coupled with the middle hub 412, causing the outer sheath 402 to retract and for the basket 416 to deploy. In an embodiment, each of the hubs 410-414 may be slidably mobile. For example, the distal hub 410 may be retracted proximally, such that the distal hub 410 slides into and/or otherwise interfaces with the middle hub 412.

Figure 9A:
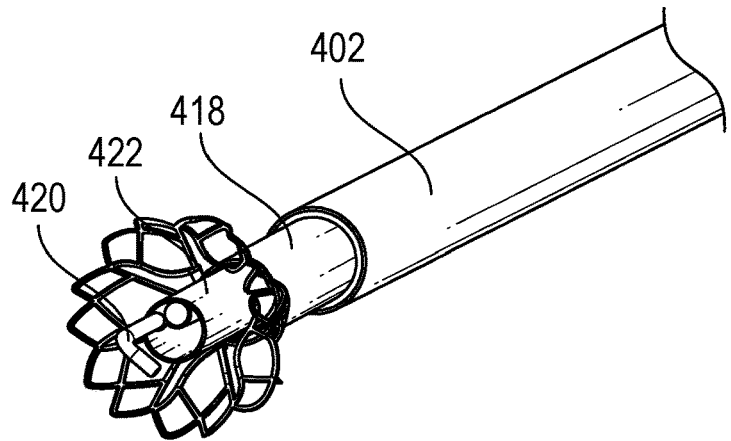
FIGS. 9A and 9C illustrate an embodiment of the dynamic stent device in an extended position, wherein the proximal hub may be pushed forward.
Figure 9B:
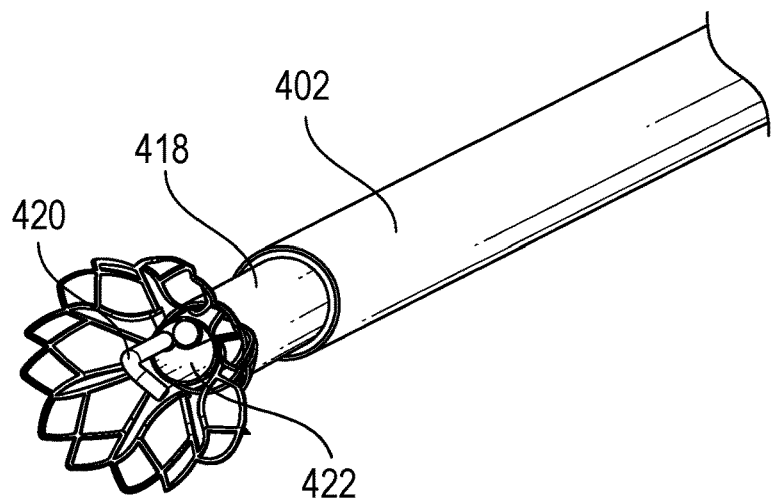
FIG. 9B illustrates an embodiment of the dynamic stent device in an acute/subacute position, before conversion to an extended position.
Figure 9C:
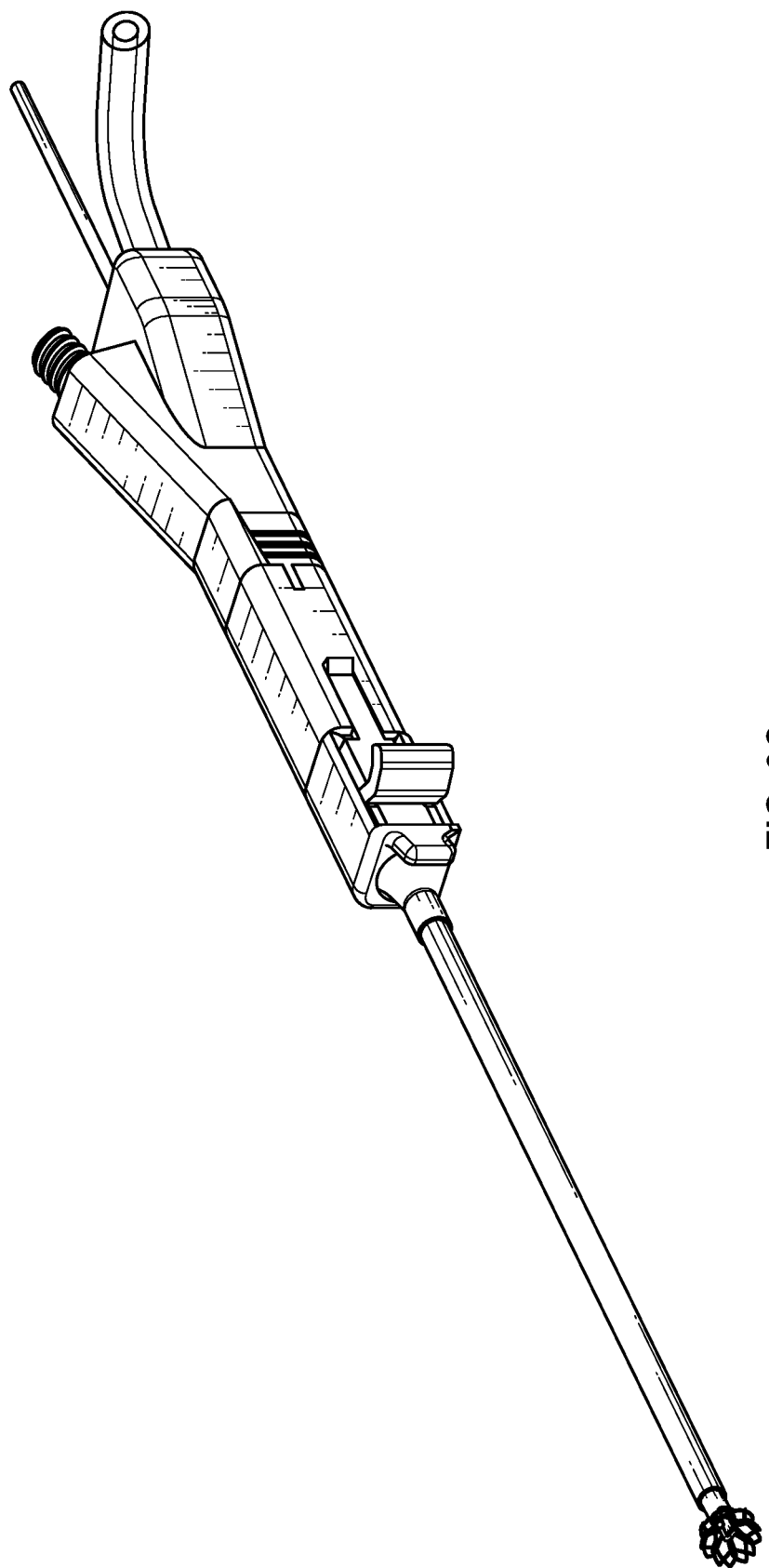

FIGS. 9A and 9C illustrate an embodiment of the dynamic stent device 100 in an extended position 408, wherein the proximal hub 414 may be pushed forward. As shown, in the extended position 408, each of the distal hub 410, the middle hub 412, and proximal hub 414 may be interfaced. Thus, the proximal hub 414 may be pushed distally to move the jet tube 420 further distal into the basket 416. In such an embodiment, the proximal hub 414 may be pushed distally, causing the proximal hub 414 to slide into and/or otherwise interface with the middle hub 412. In one embodiment, the middle hub 412 may maintain a fixed position and the proximal hub 414 and the distal hub 410 may be pushed distally and retracted proximally, respectively, to induce the aforementioned actions in the distal end of the dynamic stent device 100. In another embodiment, a slider mechanism or track may be disposed throughout the proximal hub 414, middle hub 412, and/or distal hub 410, such that each hub may be pushed or retracted along the axis of said slider mechanism or track. However, any one of the proximal hub 414, the middle hub 412, and/or the distal hub 410 may move relative to any one of the proximal hub 414, the middle hub 412, and/or the distal hub 410. As a non-limiting example, a slider mechanism or track may be disposed between the proximal hub 414 and the middle hub 412, permitting distal pushing of the proximal hub 414. Similarly, as a non-limiting example, a slider mechanism or track may be disposed between the distal hub 410 and the middle hub 412, permitting proximal retraction of the distal hub 410. As another non-limiting example, the middle hub 412 may include two pockets, each pocket sized to accept a protrusion disposed on each of the proximal hub 414 and the distal hub 410. Accordingly, in such a non-limiting example, the protrusions may reversibly enter the pockets to interface the respective hub 410/414 with the middle hub 412. Alternatively, the distal hub 410 and/or the proximal hub 414 may include pockets and/or the middle hub 412 may include protrusions.

Figure 10A:
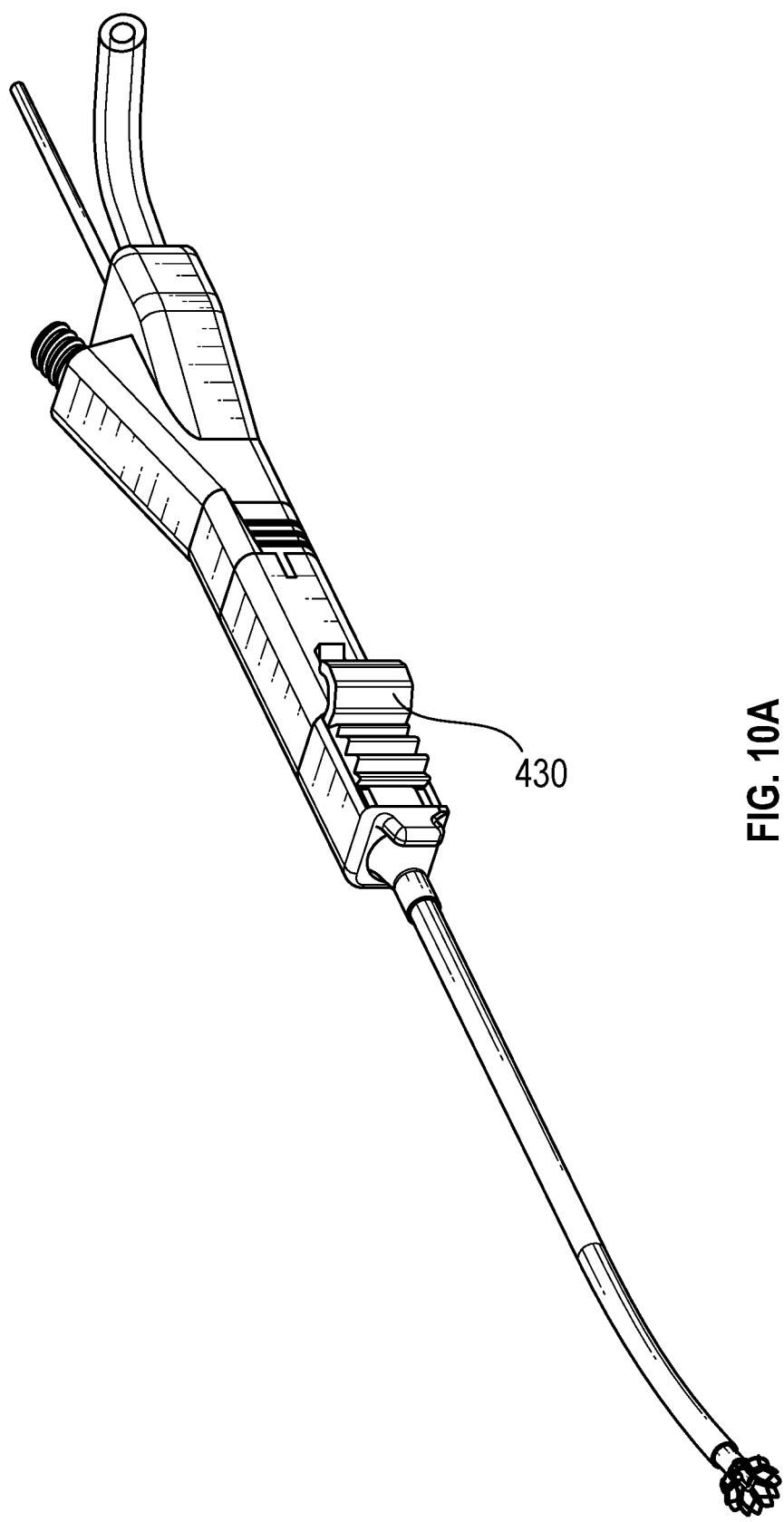
FIGS. 10A-10C illustrate an embodiment of the dynamic stent device in a deflected position.
Figure 10B:
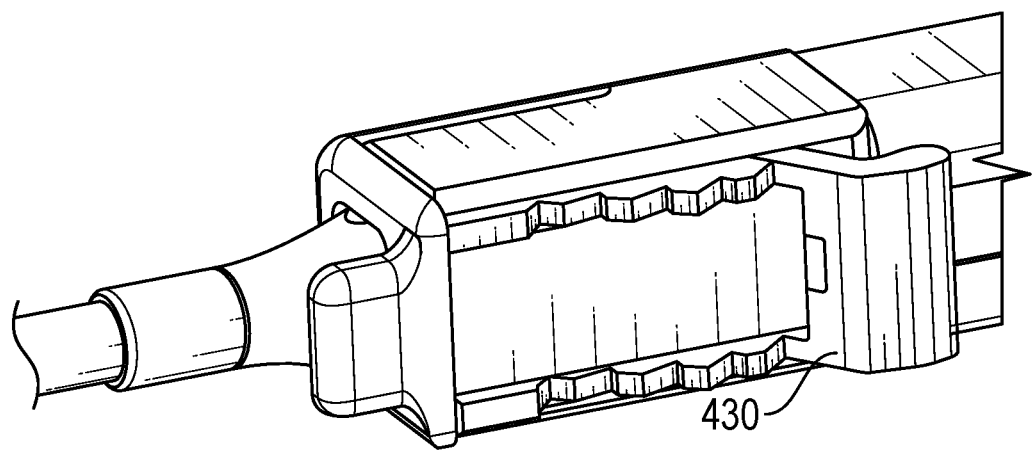
Figure 10C:
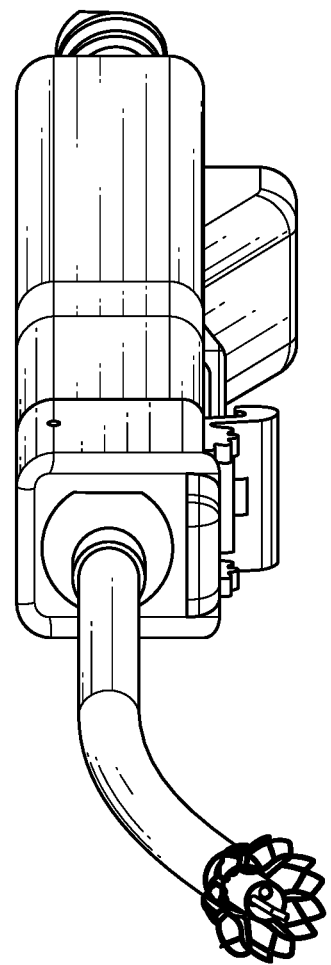

FIGS. 10A-10C illustrate an embodiment of the dynamic stent device 100 in a deflected position. As a non-limiting example, in the deflected position, the distal end of the outer sheath 402 may be deflected at an approximately fifteen degree angle. In an embodiment, the one or more pull wires 502 may be stainless steel pull wires having a diameter of approximately 0.005". However, the pull wires may be of any suitable dimensions and/or may be composed of any suitable materials. The one or more pull wires 502 may be attached to the ratchet pull handle 430, such that actuation of the ratchet pull handle 430 increases tension on at least one of the one or more pull wires 502, causing the dynamic stent device 100 to convert to the deflected position. In an embodiment, the ratchet pull handle 430 may include a plurality of ridges, wherein the plurality or ridges interface with the ratchet pull handle 430 to maintain a selected pressure on the one or more pull wires 502. In one embodiment, the ratchet pull handle 430 may be locked into position over any one of the plurality of ridges. In such an embodiment, each ridge may reflect a certain magnitude of tension in the pull wire 502 and/or a certain degree of deflection in the distal end of the dynamic stent device 100. However, in another embodiment, the ratchet pull handle 430 may be configurable in two positions: a non-actuated position as shown in FIG. 8B, and an actuated position as shown in FIG. 10B.

Figure 11:
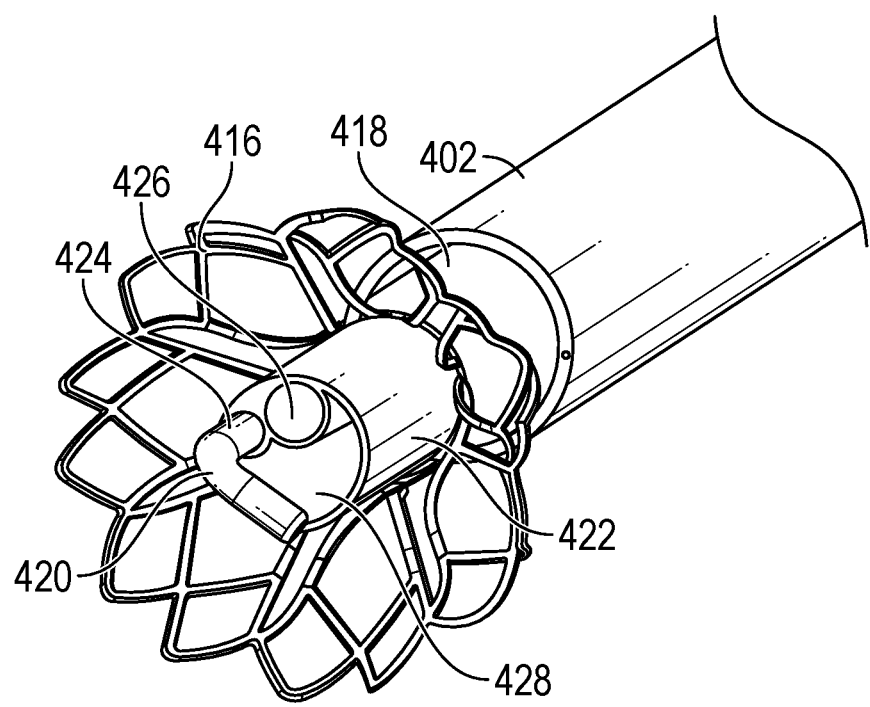
FIG. 11 illustrates an embodiment of the distal end of the dynamic stent device.

FIG. 11 illustrates an embodiment of the distal end of the dynamic stent device 100. In an embodiment, the jet tube shaft 422 is composed of thermoplastic elastomer (i.e., 72D Pebax). However, in various embodiments the jet tube shaft 422 may be composed of any suitable material, including, but not limited to, metals, plastics, rubbers, polymers, elastomers, etc. In one embodiment, the jet tube shaft 422 includes an outer diameter of approximately 0.110" and may include a wall thickness of approximately 0.005". However, in alternate embodiments, the jet tube shaft 422 may include any suitable outer diameter and/or wall thickness. The jet tube shaft 422 may include a plurality of lumens. As a non-limiting example, the jet tube shaft 422 may include three lumens. In such a non-limiting example, a first lumen (also referred to herein as a "jet tube lumen" 424) may be configured to house the jet tube 420, a second lumen (also referred to herein as a "guidewire lumen" 426) may be configured to house a guidewire, and a third lumen (also referred to herein as an "evacuation lumen" 428) may be configured for evacuation. The jet tube lumen 424 may include a diameter of 0.027" and may be configured to maintain the high-powered jet tube 420. The guidewire lumen 426 may include a diameter of 0.042" and may be sized for use with a guidewire having a diameter of 0.038". The evacuation lumen 428 may be configured for removing a high-pressure slurry, for example, from the distal end of the dynamic stent device 100 to the proximal end of the dynamic stent device 100. Referring to FIG. 11, the jet lumen 424, the guidewire lumen 426, and/or the evacuation lumen 428 may be sized such that clearance is provided to the jet tube 420. As a non-limiting example, the guidewire lumen 426 may be of a lesser cross-sectional area than the evacuation lumen 428. Further, the guidewire lumen 426 may be positioned immediately adjacent to the jet lumen 424 and may contact the sidewall of the jet tube shaft 422, such that the jet tube 420 (and resulting spray) does not interfere with the guidewire or guidewire lumen 426. Thus, the evacuation lumen 428 may include a generally semi-circular cross-sectional area to provide an adequate window for a lesser obstructed flow of fluid from the jet tube 420.

As shown in FIG. 11, the basket 416 may be used to protect the vessel or surrounding tissue from entering into the path of the high-pressure jet. In an embodiment, the stent basket shaft 418 is multi-layered, utilizing a metal braid construction for support. The stent basket shaft 418 may be composed of thermoplastic elastomer (i.e., 72D Pebax). Further, the stent basket shaft 418 may include an inner diameter of approximately 0.115" and an outer diameter of approximately 0.130". However, the stent basket shaft 418 may be of any suitable dimensions.

The outer sheath 402 may be purposed to maintain the stent basket 416 confined when the device is inserted into the body and through the vessels. Further, the outer sheath 402 may additionally facilitate a method for maneuvering the distal end of the outer sheath 402 for increased access to occlusion in large vessels by deflecting all contained shafts/lumens. In one embodiment, the outer sheath 402 is composed of a multi-lumen Polytetrafluoroethylene ("PTFE") liner and/or Nylon 12 polymer. However, the outer sheath 402 may be composed of any suitable material. The outer sheath 402 may be steerable and may include an outer diameter of approximately 0.157". Further, in such a non-limiting example, the outer sheath 402 may include an inner diameter of approximately 0.135". However, the outer sheath 402 may be of any suitable dimensions that allow entry and navigation of the desired vessels.

FIG. 12 illustrates an embodiment of a jet tube 420 and related components. The jet tube assembly may comprise a filter media 1204, an LC filter 1202, a jet tube 420, and/or a spacer tube 1206. The distal end of the jet tube 420 may include a bent portion, wherein said bent portion is disposed perpendicular to the axis of the outer sheath 402. In an embodiment, the proximal end of the jet tube 420 may be coupled to the LC filter 1202. Yet further, filter media 1204 may be disposed at the proximal end of the jet tube 420. In an embodiment, the LC filter 1202 may include a channel sized to accept the jet tube 420. In such an embodiment, a spacer tube 1206 may be disposed around the jet tube 420 when the jet tube 420 is disposed within the LC filter 1202 channel. In an embodiment, the LC filter 1202 and the filter media 1204 may be configured to remove unwanted particulates from the fluid as it is being fed into the handle 400 and later expelled through the jet tube 420. This density of the filter media 1204 may be modified based on the type of fluid and/or the characteristics of the particulates to be removed. In one embodiment, the source of fluid may be sufficiently pure and/or free of undesired particulates. In such an embodiment, the dynamic stent device 100 may function without the LC filter 1202 and/or filter media 1204.

FIGS. 13A-13B illustrate cross-sectional views of an embodiment of the jet tube 420, wherein the jet tube 420 may include a passage having a uniform inner diameter from the proximal end of the jet tube 420 to the distal end of jet tube 420. The distal end of the jet tube 420 may include a portion of jet tube 420 bent to an approximately ninety degree angle, to form the bend 434. The bend 434 may include an aperture 432, wherein the aperture 432 is facing toward the proximal end of the jet tube 420. Accordingly, fluid traveling through the jet tube 420 from the proximal end to the distal end may further be emitted through the aperture 432 such that the ejected fluid is ejected proximally. In an embodiment, the aperture 432 includes a diameter of approximately 0.005". However, the aperture 432 may include a diameter of any suitable size, such that the ejected fluid may disturb thrombus or other debris.

Figure 14:
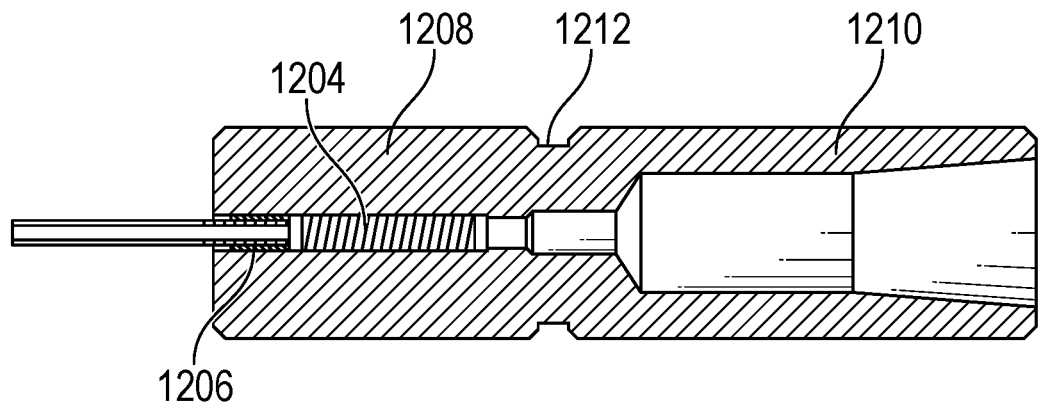
FIG. 14 illustrates a proximal end of an embodiment of the jet tube.

FIG. 14 illustrates a proximal end of an embodiment of the jet tube 420. The jet tube 420 may be coupled to an LC filter 1202. The LC filter 1202 may comprise a first portion 1208 and a second portion 1210, wherein the first portion 1208 comprises a uniform channel sized to accept the jet tube 420, the spacer tube 1206, and/or the filter media 1204, and wherein the second portion 1210 comprises a non-uniform channel sized to accept a fluid source. For example, the fluid source may be a hose or other related device configured to deliver pressurized fluid to the jet tube 420. In an embodiment, the LC filter includes an indentation 1212 demarcating the first portion 1208 from the second portion 1210. In one embodiment, before welding the jet tube 420 to the crimp fitting, a lumen extension may be installed over the jet tube 420. Accordingly, the jet tube 420, spacer tube 1206, and/or LC filter 1202 may be laser welded as to couple any of the aforementioned components.

Figures 15A, 15B:
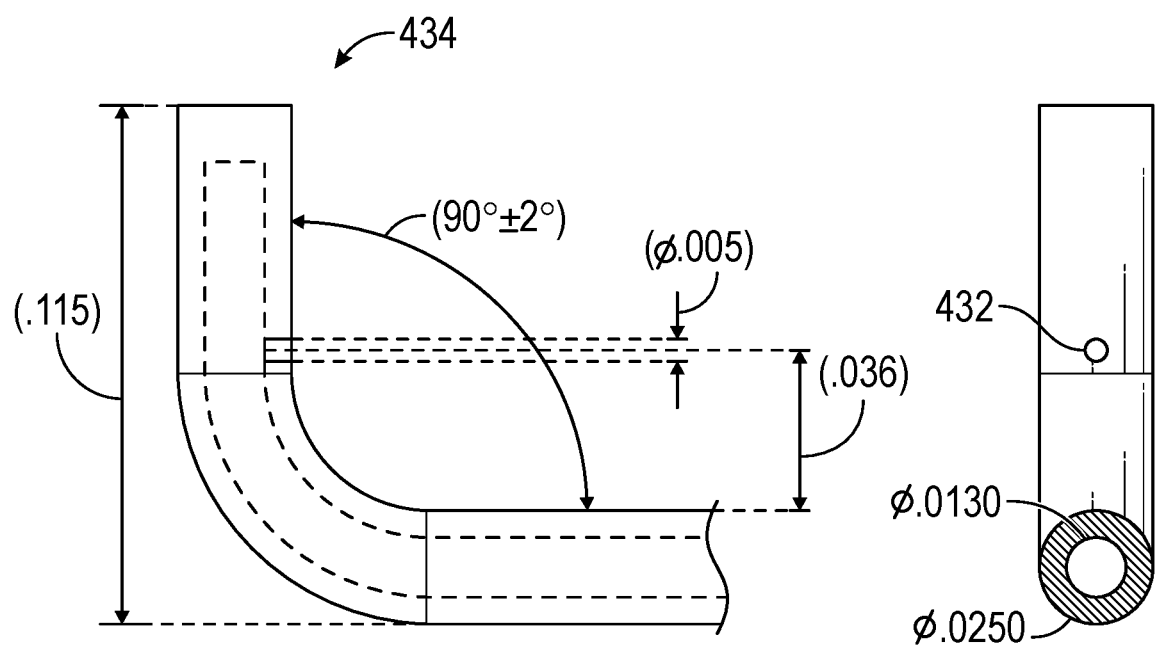
FIGS. 15A-15B illustrate a distal end of an embodiment of the jet tube.

FIGS. 15A-15B illustrate a distal end of an embodiment of the jet tube 420. In an embodiment, the bend 434 of the jet tube 420 may include a ninety degree deflection relative to the longitudinal axis of the majority of the jet tube 420. The most distal edge(s) of the bend 434 may include a bevel. The bevel may be sized to eliminate sharp edges at the most distal end of the jet tube 420. Accordingly, the bevel may decrease the likelihood of the bend 434 negatively interfering with vessel walls. In one embodiment, the aperture 432 may be formed by drilling a hole through the bend 434. In one such embodiment, the drill may pass through both sides (i.e., the distal side and proximal side of the bend 434), wherein the hole formed on the distal side of the bend may be laser welded closed.

In an embodiment, a distal locking mechanism may be disposed between the distal hub 410 and the middle hub 412. Accordingly, the distal locking mechanism may be configured to lock the position of the distal hub 410 relative to the middle hub 412. As a non-limiting example, a user may completely retract the distal hub 410 to convert the dynamic stent device 100 to an acute/subacute position 406, and may actuate the distal locking mechanism to maintain said position of the distal hub 410 and, indirectly, the position of the basket 416 relative to the outer sheath 402. In a further embodiment, the distal locking mechanism may be adapted to lock any suitable position of the distal hub 410. In such an embodiment, the distal locking mechanism may be utilized to lock the dynamic stent device 100 in positions between the closed position 404 and the acute/subacute position 406.

In an embodiment, a proximal locking mechanism may be disposed between the middle hub 412 and the proximal hub 414. Accordingly, the proximal locking mechanism may be configured to lock the position of the proximal hub 414 relative to the middle hub 412. As a non-limiting example, a user may completely push the proximal hub 414 to convert the dynamic stent device 100 to an extended position 408, and may actuate the proximal locking mechanism to maintain said position of the proximal hub 414 and, indirectly, the position of the jet tube shaft 422 relative to the outer sheath 402. In a further embodiment, the proximal locking mechanism may be adapted to lock any suitable position of the proximal hub 414. In such an embodiment, the proximal locking mechanism may be utilized to lock the dynamic stent device 100 in positions between the acute/subacute position 406 and the extended position 408. The distal locking mechanism and/or the proximal locking mechanism may be any suitable switch, button, lever, or other mechanism configured to prevent movement of the corresponding hub. For example, the locking mechanisms may be adapted to induce an unsurpassable friction between the respective hubs, such that the hubs and, indirectly, the positions of the basket 416/outer sheath 402/jet tube shaft 422 are locked. The distal locking mechanism and/or the proximal locking mechanism may be disposed on any suitable hub and/or between any suitable hubs.

Although this disclosure contemplates deployed and undeployed states of the basket 416; closed position 404, acute/subacute position 406, extended position 408, and/or enhanced extended position 602 of the dynamic stent device 100; and deflected and straight configurations, the device 100 and components thereof may be placed into any of the aforementioned configurations or configurations therebetween by manipulation of the device 100 as described herein. Thus, the device 100 may be capable of exhibiting, and may be manipulated into, elements of any of the aforementioned configurations simultaneously. As a non-limiting example, the device 100 is capable of complete retraction of the distal hub 410 to convert said device 100 to the acute/subacute position and the device 100 is capable of partial retraction of the distal hub 410 to partially unsheathe the basket 416.

Various elements, which are described herein in the context of one or more embodiments, may be provided separately or in any suitable subcombination. Further, the processes described herein are not limited to the specific embodiments described. For example, the processes described herein are not limited to the specific processing order described herein and, rather, process blocks may be re-ordered, combined, removed, or performed in parallel or in serial, as necessary, to achieve the results set forth herein.

It will be further understood that various changes in the details, materials, and arrangements of the parts that have been described and illustrated herein may be made by those skilled in the art without departing from the scope of the following claims.

All references, patents and patent applications and publications that are cited or referred to in this application are incorporated in their entirety herein by reference. Finally, other implementations of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A medical device comprising:
   a handle comprising:
   a distal hub;
   a proximal hub; and
   a middle hub disposed between the distal hub and the proximal hub; and
   an outer sheath coupled with the distal hub, the distal hub configured to translate movement of the distal hub to movement of the outer sheath;
   a basket configurable in a deployed state and an undeployed state;
   a jet tube shaft coupled with the proximal hub, the jet tube shaft coaxial to the outer sheath, the jet tube shaft comprising:
   a jet tube comprising an aperture configured to expel a fluid;
   a jet tube lumen sized to accept the jet tube; and
   an evacuation lumen.

2. The medical device of claim 1, the proximal hub configured to translate movement of the proximal hub to movement of the jet tube shaft.

3. The medical device of claim 1, the jet tube shaft further comprising a guidewire lumen sized to accept a guidewire.

4. The medical device of claim 3, wherein the jet tube lumen comprises a jet tube lumen cross-sectional area, the evacuation lumen comprises an evacuation lumen cross-sectional area, and the guidewire lumen comprises a guidewire lumen cross-sectional area; and wherein the evacuation lumen cross-sectional area is greater than the guidewire lumen cross-sectional area, and the guidewire lumen cross-sectional area is greater than the jet tube lumen cross-sectional area.

5. The medical device of claim 1, the handle further comprising a slider operably coupled to the jet tube, wherein the slider is configured to translate movement of the slider into movement of the jet tube.

6. The medical device of claim 1, the jet tube further comprising a bend orthogonal to the jet tube shaft, wherein the aperture is disposed on the bend, and wherein the aperture is configured to expel fluid toward the evacuation lumen.

7. The medical device of claim 6, wherein the bend is disposed proximal to a leading edge of the basket.

8. The medical device of claim 1, wherein the basket is composed of nitinol.

9. The medical device of claim 1, the handle further comprising a ratchet coupled to one or more pull wires, wherein the one or more pull wires are coupled to a distal end of the outer sheath, and wherein actuation of the ratchet induces deflection in the distal end of the outer sheath via the one or more pull wires.

10. The medical device of claim 9, the outer sheath further comprising one or more pull wire channels disposed in a sidewall of the outer sheath, wherein the one or more pull wire channels are sized to accept each of the one or more pull wires.

11. The medical device of claim 1, wherein the basket is a mesh structure.

12. The medical device of claim 11, wherein, in the undeployed state, the basket is configured to conform to the outer sheath, and wherein, in the deployed state, the basket is configured to radially expand.

13. The medical device of claim 12, the basket further comprising a leading edge, wherein, in the deployed state, the leading edge is concave, and wherein, in the deployed state, the basket is conical.

14. The medical device of claim 1, the basket further comprising one or more markers, wherein the one or more markers are configured to be radiopaque in fluoroscopy and radiography.

15. The medical device of claim 1, the jet tube comprising a bevel disposed on a distal end of the jet tube.

16. A medical device comprising:
 a handle comprising:
  a distal hub;
  a slider;
  a proximal hub; and
  a middle hub disposed between the distal hub and the proximal hub; and
 an outer sheath coupled with the distal hub;
 a basket configurable in a deployed state and an undeployed state;
 a jet tube shaft coupled with the proximal hub, the jet tube shaft coaxial to the outer sheath, the jet tube shaft comprising:
  a jet tube comprising an aperture configured to expel a fluid;
  a jet tube lumen sized to accept the jet tube; and
  an evacuation lumen; and
 wherein the slider is operably coupled to the jet tube, and wherein the slider is configured to translate movement of the slider into movement of the jet tube.

17. A medical device comprising:
 a handle comprising:
  a distal hub;
  a ratchet coupled to one or more pull wires;
  a proximal hub; and
  a middle hub disposed between the distal hub and the proximal hub; and
 an outer sheath coupled with the distal hub, wherein the one or more pull wires are coupled to a distal end of the outer sheath, and wherein actuation of the ratchet induces deflection in the distal end of the outer sheath via the one or more pull wires;
 a basket configurable in a deployed state and an undeployed state;
 a jet tube shaft coupled with the proximal hub, the jet tube shaft coaxial to the outer sheath, the jet tube shaft comprising:
  a jet tube comprising an aperture configured to expel a fluid;
  a jet tube lumen sized to accept the jet tube; and
  an evacuation lumen.

* * * * *